United States Patent [19]

Doehner, Jr.

[11] Patent Number: 5,144,041

[45] Date of Patent: Sep. 1, 1992

[54] PROCESS FOR THE PREPARATION OF 2-ARYL-1-SUBSTITUTED-5-(TRI-FLUOROMETHYL) PYRROLE COMPOUNDS USEFUL AS INSECTICIDAL, ACARICIDAL AND NEMATOCIDAL AGENTS AND AS INTERMEDIATES FOR THE MANUFACTURE OF SAID AGENTS

[75] Inventor: Robert F. Doehner, Jr., East Windsor, N.J.

[73] Assignee: American Cyanamid Company, Stamford, Conn.

[21] Appl. No.: 854,165

[22] Filed: Mar. 20, 1992

Related U.S. Application Data

[63] Continuation-in-part of Ser. No. 634,286, Dec. 26, 1990.

[51] Int. Cl.$^5$ .................. C07D 207/30; C07D 207/34
[52] U.S. Cl. ..................................... 548/531; 548/557; 548/561
[58] Field of Search .................. 548/531, 557, 561

[56] References Cited

U.S. PATENT DOCUMENTS 5,030,735 7/1991 Addor et al. ........................ 548/531

OTHER PUBLICATIONS

CA 111:194576w Preparation . . . pesticides, Brown et al., p. 755, 1989.
CA 111:111037x Preparation . . . molluscicides, Herman et al., p. 271, 1989.
CA 113:115076y Preparation . . . fungi, Froyd et al., p. 674, 1990.
CA 115:114396g A facile . . . multiple bond, Tian et al., 1991.
Benages et al., J. Org. Chem., 43 (22):4273–4276 (1978).
Chemical Abstracts, 111: 11037x, Sep. 25, 1989, Herman et al, p. 271.

*Primary Examiner*—Mary C. Lee
*Assistant Examiner*—Joseph K. McKane
*Attorney, Agent, or Firm*—Peggy A. Climenson

[57] ABSTRACT

A method for the preparation of insecticidal arylpyrroles, and intermediates for the manufacture of insecticidal arylpyrroles, via a single step 1,3-dipolar cycloaddition process is provided.

5 Claims, No Drawings

PROCESS FOR THE PREPARATION OF 2-ARYL-1-SUBSTITUTED-5-(TRIFLUOROMETHYL) PYRROLE COMPOUNDS USEFUL AS INSECTICIDAL, ACARICIDAL AND NEMATOCIDAL AGENTS AND AS INTERMEDIATES FOR THE MANUFACTURE OF SAID AGENTS

This is a continuation-in-part of copending application Ser. No. 07/634,286 filed on Dec. 26, 1990.

BACKGROUND OF THE INVENTION

Arylpyrrole compounds and their use as insecticidal, acaricidal and nematicidal agents are described in copending U.S. application Ser. No. 392,495 filed on Aug. 11, 1989 which is a continuation-in-part of U.S. application Ser. No. 208,841 on Jun. 23, 1988 which is a continuation-in-part of U.S. application Ser. No. 079,545 filed on Jul. 29, 1987, now abandoned. A process for the preparation of 2-aryl-5-(trifluoromethyl)-pyrrole compounds via an azalactone intermediate is described in U.S. Pat. No. 5,030,735. A method for the preparation of insecticidal arylpyrrole compounds via a pyrroline intermediate is described in copending U.S. application Ser. No. 634,288, filed on Dec. 26, 1990.

In view of the fundamental utility of certain arylpyrrole compounds for the control of insect, acarid and nematode pests and for the protection of important agronomic crops from the ravages of said pests, more methods of preparation of said arylpyrrole compounds are needed. It is an object of this invention to provide an efficient and effective single step process for the preparation of insecticidal 2-aryl-1-substituted-5-(trifluoromethyl)pyrrole compounds.

SUMMARY OF THE INVENTION

The present invention relates to a process for the preparation of arylpyrrole compounds of formula I wherein
A is $C_1-C_6$ alkyl, phenyl, phenyl substituted with halogen or $C_1-C_6$ alkyl substituted with phenyl;
W is CN, $NO_2$ or $COOR_1$;
L is hydrogen or halogen and
M and R are each independently hydrogen, $C_1-C_4$ alkyl, $C_1-C_4$ alkoxy, $C_1-C_4$ alkylthio, $C_1-C_4$ alkylsulfinyl, $C_1-C_4$ alkylsulfonyl, CN, $NO_2$, halogen, $CF_3$, $R_2CF_2Z$, $R_3CO$ or $NR_4R_5$ and when M and R are on adjacent positions they may be taken together with the carbon atoms to which they are attached to form a ring in which MR represents the structure
$-OCH_2O-$, $-OCF_2O-$ or $-CH=CH-CH=CH-$;
Z is $S(O)_n$ or O;
$R_1$ is $C_1-C_6$ alkyl, $C_3-C_6$ cycloalkyl or phenyl;
$R_2$ is hydrogen, F, $CHF_2$, CHFCl or $CF_3$;
$R_3$ is $C_1-C_4$ alkoxy or $NR_3R_4$;
$R_4$ is hydrogen or $C_1-C_4$ alkyl;
$R_5$ is hydrogen, $C_1-C_4$ alkyl or $R_6CO$;
$R_6$ is hydrogen or $C_1-C_4$ alkyl; and
n is an integer of 0, 1 or 2 which comprises reacting a 2-arylamino acid compound of formula II wherein A, L, M and R are as defined above with about one molar equivalent of a 1,3-dipolarophile of formula III wherein X is Cl or Br and W is defined above and at least one molar equivalent of an organic base in the presence of an acid anhydride and a solvent at an elevated temperature.

The product arylpyrrole compounds of formula I are highly useful as insecticidal, acaricidal and nematocidal agents and, further, are important intermediates in the manufacture of certain insecticidal arylpyrrole compounds. Said utility is described in copending U.S. application Ser. No. 392,495, filed on Aug. 11, 1989, and U.S. application Ser. No. 634,288, filed on Dec. 26, 1990.

Compounds of formula II and a method for the preparation thereof are described in copending U.S. application Ser. No. 06/634,287 filed concurrently herewith and incorporated herein by reference thereto.

DESCRIPTION OF THE INVENTION

Advantageously, it has been found that a 2-arylamino acid compound of formula II efficiently undergoes a regiospecific, one step 1,3-cycloaddition to form a 5-membered heterocyclic compound of formula I.

Hence, arylpyrrole compounds of formula I may be prepared by reacting a 2-arylamino acid compound of formula II with about one molar equivalent of a 1,3-dipolarophile of formula III and at least one molar equivalent of an organic base in the presence of an acid anhydride and a solvent, preferably at an elevated temperature. The reaction is shown in flow diagram I

FLOW DIAGRAM I

-continued
FLOW DIAGRAM I

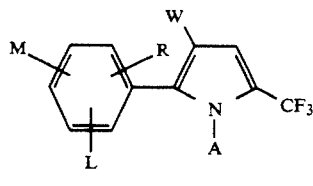

(I)

Solvents that may be used in the method of invention include aprotic organic solvents for example nitriles such as acetonitrile; esters such as ethyl acetate, methyl propionate and the like; ethers such as diethyl ether, tetrahydrofuran, dioxane, ethylene glycol dimethyl ether and the like; halogenated hydrocarbons such as methylene chloride, 1,2-dichloroethane, chloroform, 1,1,1-trichloroethane, carbon tetrachloride and the like; carboxylic acid amides such as N,N-dimethylformamide, N-methylpyrrolidinone and the like; sulfoxides such as dimethyl sulfoxide; sulfones such as tetramethylene sulfone; aromatic hydrocarbons such as benzene, toluene, xylene and the like; halogenated aromatic hydrocarbons such as chlorobenzene, o-dichlorobenzene and the like. One of the preferred organic solvents is acetonitrile. Acid anhydrides suitable for use in the method of invention are lower-alkyl anhydrides such as acetic anhydride. Among the organic bases that may be used in the inventive method are pyridine, morpholine, tri($C_1$-$C_4$)alkylamine, hexamethylenetetramine, dimethylamino pyridine and the like. A preferred organic base is a tri($C_1$-$C_4$)alkylamine such as triethylamine.

The rate of formation of the formula I arylpyrrole is directly related to the reaction temperature. Lower reaction temperatures result in increased reaction time. Advantageously, it has been found that elevated temperatures such as about 30°-100° C., preferably 50°-90° C. result in efficient product formation.

Compounds of formula II may be prepared via condensation of the appropriate arylaldehyde with cyanide and a suitable amine to form the corresponding amino nitrile, which is acetylated and hydrolyzed to form the amino acid intermediate of formula III, which is then trifluoroacetylated to obtain the desired formula II compound as shown in Flow Diagram II.

FLOW DIAGRAM II

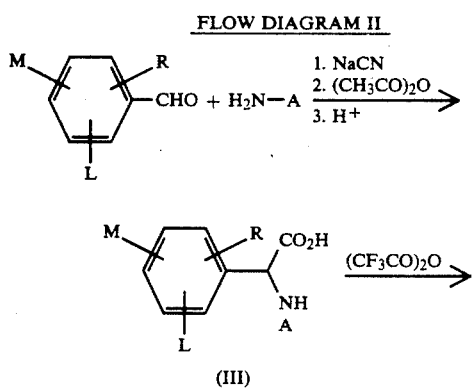

-continued
FLOW DIAGRAM II

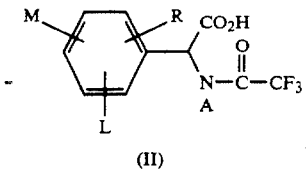

(II)

Compounds of formula II may also be prepared via trifluoroacetylation of the appropriate arylglycine precursor followed by alkylation of the thus-obtained compound using an alkylating agent such as a lower alkylhalide. Using methyliodide as the alkylating agent, the reaction sequence is illustrated in flow diagram III.

FLOW DIAGRAM III

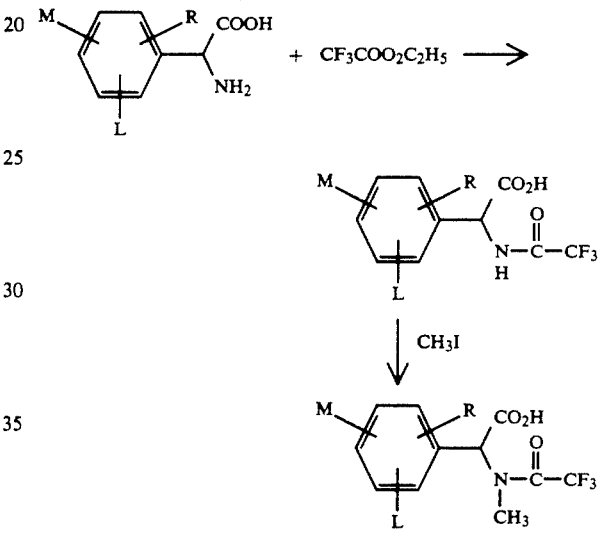

Compounds of formula I are useful for the control of insect, acarid and nematode pests and for protecting growing and harvested crops from the ravages of said pests. Compounds of formula I are also useful as key intermediates in the manufacture of certain insecticidal arylpyrrole compounds. For example, compounds of formula I may be halogenated to afford the corresponding 2-aryl-4-halopyrrole insecticidal agents of formula IV as shown in flow diagram IV.

FLOW DIAGRAM IV

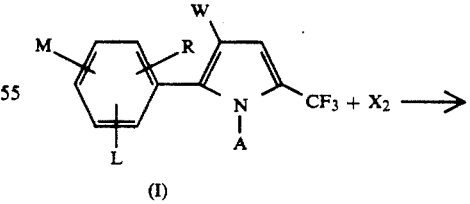

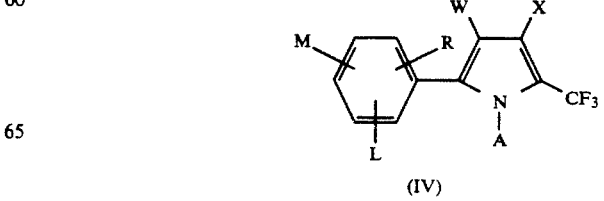

(IV)

By varying the substituents A, W, L, M and R and the halogen, $X_2$, numerous possible insecticidal arylpyrroles may be prepared from the key intermediate compound of formula I.

In order to facilitate a further understanding of the invention, the following examples are set forth primarily for the purpose of illustrating certain more specific details thereof. The invention is not to be limited thereby except as defined in the claims. The term HPLC designates high pressure liquid chromatography.

EXAMPLE I

Preparation of 2-(p-Chlorophenyl)-1-methyl-5-(trifluoromethyl)pyrrole-3-carbonitrile

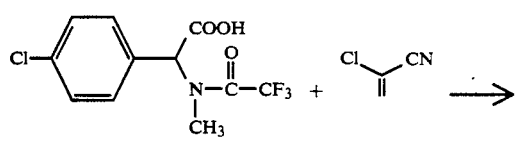

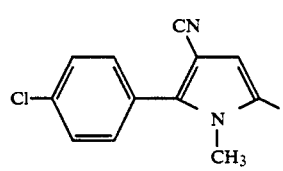

A mixture of 2-(p-chlorophenyl)-N-(trifluoroacetyl)-sarcosine (147.7 g, 0.50 mol) in acetonitrile is treated dropwise with α-chloroacrylonitrile (54.7 g, 0.62 mol) and acetic anhydride (153 g, 1.5 mol), stirred vigorously, treated dropwise with triethylamine (58.1 g, 0.57 mol) at 56°–60° C. over a 1¼ hour period, heated at 60° C. for 16 hours and concentrated in vacuo to give a residue. The residue is partitioned between ethyl acetate and water. The organic phase is concentrated in vacuo to afford an amber solid residue. Said solid is purified by flash chromatography (silica; ethyl acetate/hexanes) and recrystallized from methanol to give the title product as a pale yellow solid, mp 129.5°–130.5° C.

EXAMPLE 2

Preparation of 2-Aryl-1-(substituted)-5-(trifluoromethyl)pyrrole compounds

Using essentially the same procedure described in Example 1 and substituting the appropriate 2-aryl-N-(trifluoroacetyl)substrate and suitable 1,3-dipolarophile yields the title products shown in Table I.

TABLE I

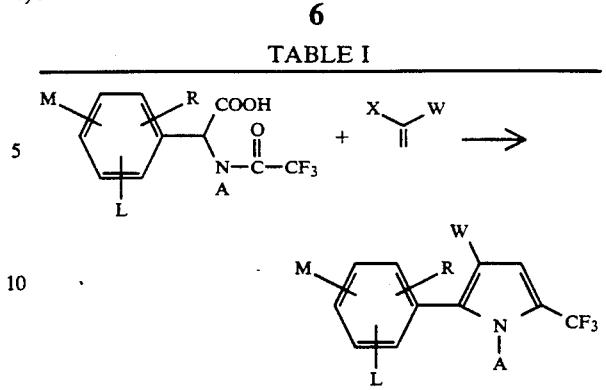

| L | M | R | A | W | X | mp °C. |
|---|---|---|---|---|---|---|
| 3-Cl | 4-Cl | H | CH₃ | NO₂ | Cl | 100–103 |
| H | 4-Cl | H | C₆H₅Cl-p- | CN | Cl | 135–137 |
| H | 4-Cl | H | CH₂C₆H₅ | CN | Cl | 96–98 |
| H | 4-CF₃ | H | CH₃ | CN | Cl | — |
| H | 4-F | H | CH₃ | CN | Cl | — |
| 2-Cl | 3-Cl | H | CH₃ | CN | Cl | — |

EXAMPLE 3

Preparation of 2-(p-Chlorophenyl-4-bromo-1-methyl-5-(trifluoromethyl)pyrrole-3-carbonitrile

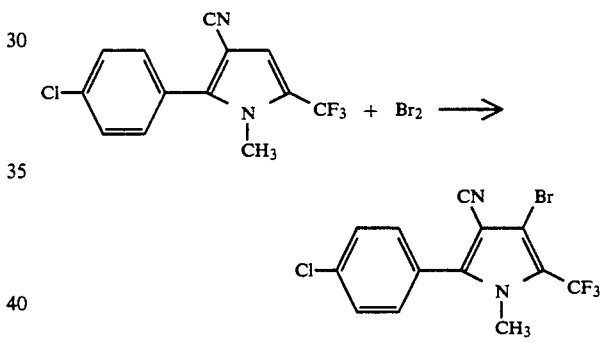

A solution of 2-(p-chlorophenyl)-1-methyl-5-(trifluoromethyl)pyrrole-3-carbonitrile (5.70 g, 0.02 mol) in chlorobenzene is treated with bromine (3.52 g, 0.022 mol), heated at 80° C. for 20 hours, cooled to room temperature, treated with additional bromine (3.52 g, 0.022 mol) and heated at 100° C. until reaction is complete by HPLC analysis. The reaction mixture is cooled to room temperature and diluted with ethyl acetate and water. The organic phase is washed with aqueous sodium metabisulfite, dried (MgSO₄) and concentrated in vacuo to afford a solid residue. The residue is recrystallized from ethyl acetate/heptane to give the title product as a white solid, 6.50 g (89.4% yield), mp 126°–129° C.

I claim:

1. A process for the preparation of a compound of formula I

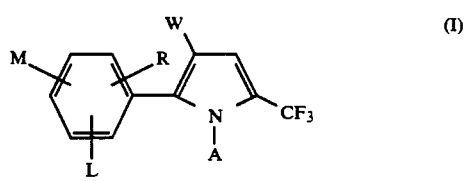

wherein

A is $C_1$-$C_6$ alkyl, phenyl, phenyl substituted with halogen or $C_1$-$C_6$ alkyl substituted with phenyl;

W is CN, $NO_2$ or $COOR_1$;

L is hydrogen or halogen and

M and R are each independently hydrogen, $C_1$-$C_4$ alkyl, $C_1$-$C_4$ alkoxy, $C_1$-$C_4$ alkylthio, $C_1$-$C_4$ alkylsulfinyl $C_1$-$C_4$ alkylsulfonyl, CN, $NO_2$, halogen, $CF_3$, $R_2CF_2Z$, $R_3CO$ or $NR_4R_5$ and when M and R are on adjacent positions they may be taken together with the carbon atoms to which they are attached to form a ring in which MR represents the structure $-OCH_2O-$, $-OCF_2O-$ or $-CH=CH-CH=CH-$;

Z is $S(O)_n$ n or O;

$R_1$ is $C_1$-$C_6$ alkyl, $C_3$-$C_6$ cycloalkyl or phenyl;

$R_2$ is hydrogen, F, $CHF_2$, CHFCl or $CF_3$;

$R_3$ is $C_1$-$C_4$ alkyl, $C_1$-$C_4$ alkoxy or $NR_4R_5$;

$R_4$ is hydrogen or $C_1$-$C_4$ alkyl;

$R_5$ is hydrogen, $C_1$-$C_4$ alkyl or $R_6CO$;

$R_6$ is hydrogen or $C_1$-$C_4$ alkyl; and n is an integer of 0, 1 or 2 which comprises reacting a compound of formula II

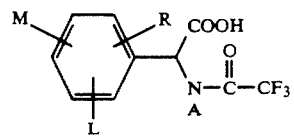

wherein A, L, M and R are as defined above with about one molar equivalent of a compound of formula III

wherein X is Cl or Br and W is described above and at least one molar equivalent of an organic base in the presence of an acid anhydride and a solvent at an elevated temperature.

2. The process according to claim 1 wherein the temperature is about 30° to 100° C.

3. The process according to claim 1 wherein the organic base is tri($C_1$-$C_4$ alkyl)amine and the solvent is acetonitrile.

4. The process according to claim 3 wherein the organic base is triethylamine.

5. The process according to claim 1 wherein X is Cl and W is CN or $NO_2$.

* * * * *